United States Patent [19]

Schulte-Elte et al.

[11] 4,438,283
[45] Mar. 20, 1984

[54] PROCESS FOR THE PREPARATION OF HYDROXY-KETONES

[75] Inventors: Karl H. Schulte-Elte, Onex; Roger L. Snowden, Grand-Lancy; Bernard L. Muller, Geneva, all of Switzerland

[73] Assignee: Firmenich SA, Geneva, Switzerland

[21] Appl. No.: 391,996

[22] Filed: Jun. 25, 1982

[30] Foreign Application Priority Data

Jul. 24, 1981 [CH] Switzerland ............... 4842/81

[51] Int. Cl.³ .............................................. C07C 45/51
[52] U.S. Cl. ................................................ 568/403
[58] Field of Search ................. 568/403, 405, 361, 393

[56] References Cited

U.S. PATENT DOCUMENTS 3,887,625  6/1975  Schulte-Elte ............... 568/361
3,976,700  8/1976  De Simone ................. 568/393

FOREIGN PATENT DOCUMENTS 21769    7/1981  European Pat. Off. ......... 568/403
2305140  8/1973  Fed. Rep. of Germany ..... 568/403

OTHER PUBLICATIONS

Ishikawa et al., Chem. Abst., vol. 95, #61392n, (1981).

Primary Examiner—James H. Reamer
Attorney, Agent, or Firm—Pennie & Edmonds

[57] ABSTRACT

Hydroxy-ketones having formula

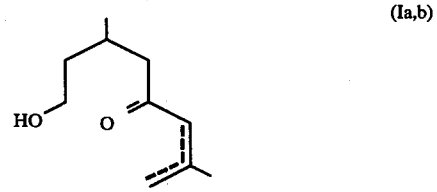

(Ia,b)

possessing a double bond in one of the positions indicated by the dotted lines, are prepared starting from a diallyl carbinol of formula

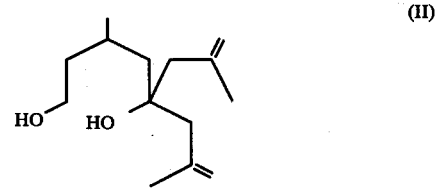

(II)

Hydroxy-ketones (Ia, b) are useful as intermediates for the preparation of rose oxide.

4 Claims, No Drawings

PROCESS FOR THE PREPARATION OF HYDROXY-KETONES

BRIEF SUMMARY OF THE INVENTION

The instant invention relates to a process for the preparation of useful intermediates for the synthesis of rose oxide, a valuable perfuming ingredient. It relates particularly to a process for preparing hydroxy-ketones of formula

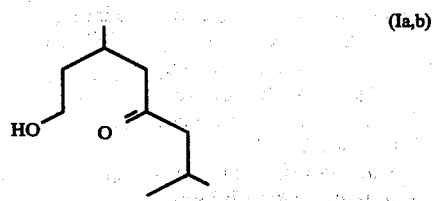
(Ia,b)

possessing a double bond in one of the positions indicated by the dotted lines, which process comprises treating with a strong base in an inert organic solvent a diallyl carbinol of formula

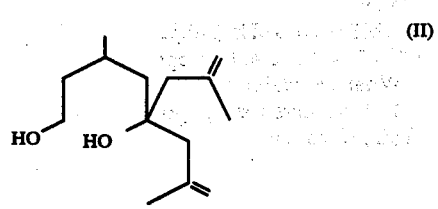
(II)

BACKGROUND OF THE INVENTION

2-[2-Methyl-prop-1-en-1-yl]-4-methyl-tetrahydropyran, a terpenic ether of formula

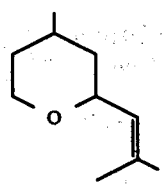

better known by its common designation of "rose oxide", is a particularly valuable ingredient for perfumery.

Ever since its discovery in 1960 [cf. Swiss Pat. No. 395,406], numerous publications relative to its preparation have appeared in scientific journals and in the patent literature.

Most of the known methods include the use of acyclic intermediates or the introduction of the 2-isobutenyl substituent in the preliminary formed pyran ring. A different synthetic approach, starting from 3-methyl-but-2-en-1-al and 2-methyl-but-1-en-4-ol, was suggested by J. P. H. Tyman and B. J. Willis [cf. Tetrahedron Letters, 51, 4507 (1970)] which method can be illustrated by the following reaction pathway:

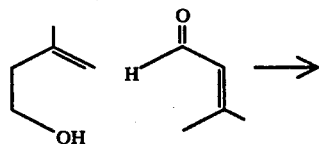

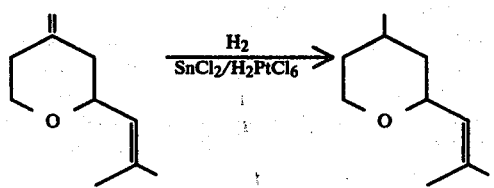

According to the above cited authors the reduction of the methylene intermediate, or rose dehydroxide, is carried out by hydrogenation in a homogeneous phase in the presence of tin$^{II}$ chloride and hexachloropatinic acid. It was thus possible to obtain a mixture comprising about 91% of cis isomer and about 9% trans isomer.

The International Application No. WO 79/00509 relates to a process destined to prepare rose oxide under the form of a mixture containing eminently the cis isomer, which process makes also use of 3-methyl-but-2-en-1-al and 2-methyl-but-1-en-4-ol as starting materials but contemplates an additional isomerization step by means of an acidic agent.

The commercial interest presented by rose oxide has further stimulated the search for alternative synthetic routes. This invention provides a novel means for its preparation.

PREFERRED EMBODIMENTS OF THE INVENTION

As described above, the process of the instant invention provides a process for the preparation of hydroxy-ketones (I), which compound can be converted conveniently into rose oxide according to the method illustrated by the following reaction pathway:

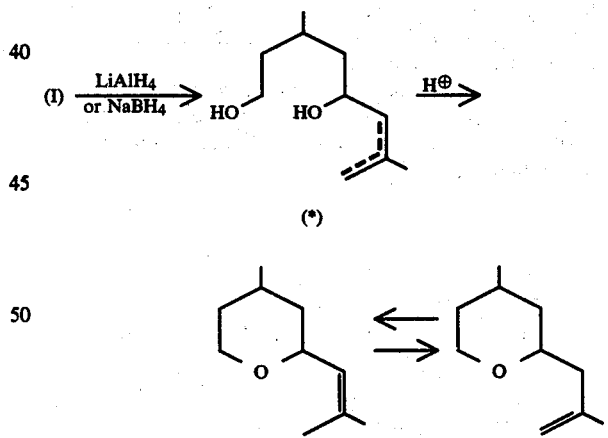

(*)cf. Synthesis 27 (1980) and Bull. Chem. Soc. Japan 54, 776 (1981).

Diallyl carbinol (II), the starting material of the presently disclosed process, can be obtained by a Grignard-type reaction from 3-methyl-valerolactone and a methallyl-magnesium halide according to the following:

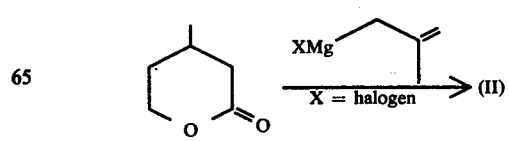

The reaction which characterizes the process of the invention consists formally in an anionic splitting promoted by a strong base. To this end, mineral or organic bases such as alkali metal hydrides, alkoxides or hydroxides, preferably sodium or potassium derivatives, are used. Among the said bases one may cite especially sodium or potassium hydride, sodium or potassium tert-butoxide, sodium tert-amylate and sodium methoxide or ethoxide.

The choice among the bases cited above is determined by considerations of economy, safety and occupational health. As a consequence alkoxides are preferred to hydrides and among them potassium or sodium tert-butoxide is preferably used.

It could be established that the proportion of the base used must be equal to or higher than the required stoechiometric quantity. In reality, the best yields were achieved by the use of an excess of base.

The reaction times observed are relatively short. Of course, the temperature exerts a determining influence on the reaction time. The process, which is in itself exothermic, can be carried out at a temperature near the room temperature. Values of between about 20° and 90° C. are preferred, whereas at temperatures below the said range the reaction time becomes too long. Temperature values higher than the above given upper limit can be applied with success by carrying out the reaction in aprotic solvents, for instance in the presence of methylpyrrolidone.

As described above, the reaction is effected in an inert organic solvent. Suitable solvents include ethers such as tetrahydrofuran or diisopropylether, amides such as dimethylformamide or phosphorus hexamethyl-triamide, an aromatic hydrocarbon, for instance benzene or toluene, an alcohol such as ethyl alcohol or tert-butanol, or even methyl-pyrrolidone or dimethylsulfoxide. Mixtures of the above cited solvents can also be used. According to a preferred embodiment, potassium tert-butoxide is used as base and dimethylformamide or a mixture of dimethylformamide with tetrahydrofuran can be used as a solvent.

Under the reaction conditions used, hydroxy-ketones of formula (Ia, b) obtained by the process of the instant invention are in equilibrium with their corresponding hemi-acetals (Ic, d):

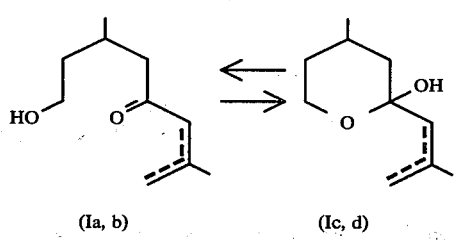

(Ia, b)    (Ic, d)

We have observed in fact that by the process of the invention we obtained mixtures containing variable amounts of eminently four compounds, to wit 3,7-dimethyl-5-oxo-oct-6-enol, 3,7-dimethyl-5-oxo-oct-7-enol, tetrahydro-4-methyl-2-(2-methyl-prop-2-enyl)-2-(2H)-pyranol and tetrahydro-4-methyl-2-(2-methyl-prop-1-enyl)-2(2H)-pyranol. 3,7-Dimethyl-5-oxo-oct-6-enol is formed in major quantity (ca. 80%).

The invention is illustrated by but not limited to the following example wherein the temperatures are indicated in degrees centigrade.

EXAMPLE 22.6 g (0.1 M) of 3,7-dimethyl-5-hydroxy-5-(2-methyl-prop-2-enyl)-oct-7-enol and 22 g (0.2 M) of potassium tert-butoxide in 100 ml of dimethylformamide were heated while stirring to 80° under nitrogen atmosphere. After cooling, the reaction mixture was poured into a solution of glacial acetic acid (22 g) and 100 g of ice, whereupon it was taken up with 200 ml of petrol ether. The organic phase was washed with successively hydrochloric acid, water and a diluted solution of NaOH until neutrality.

The evaporation of the organic phase gave 17 g of a residue consisting of about 85% of 3,7-dimethyl-5-oxo-oct-6-enol and 3,7-dimethyl-5-oxo-oct-7-enol together with about 15% of the hemi-acetals of formulae (Ic) and (Id).

IR: 3400, 3080, 1715, 1675, 1640, 1620, 1050–1100 and 895 cm$^{-1}$.

NMR (60 MHz): 0.85–1.05; 1.72 and 1.18; 3.08; 3.4–4.2; 4.8 and 4.95 δ ppm.

What we claim is:

1. A process for the preparation of hydroxy-ketones having formula

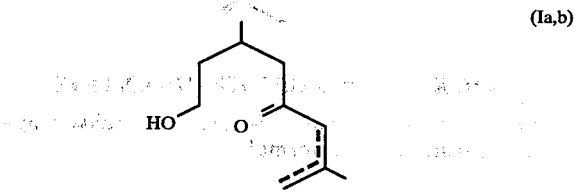

(Ia,b)

possessing a double bond in one of the positions indicated by the dotted lines which comprises treating with at least a stoichiometric amount of a strong base, in an inert organic solvent, a diallyl carbinol of formula (II)

2. A process according to claim 1 wherein the strong base is potassium tert-butoxide.

3. A process according to claim 2, wherein the raction is carried out in dimethylformamide and at a temperature of between 20° and 90° C.

4. A process according to claim 1, wherein the strong bases is a metal hydride, alkoxide or hydroxide.

* * * * *